Figure 1:
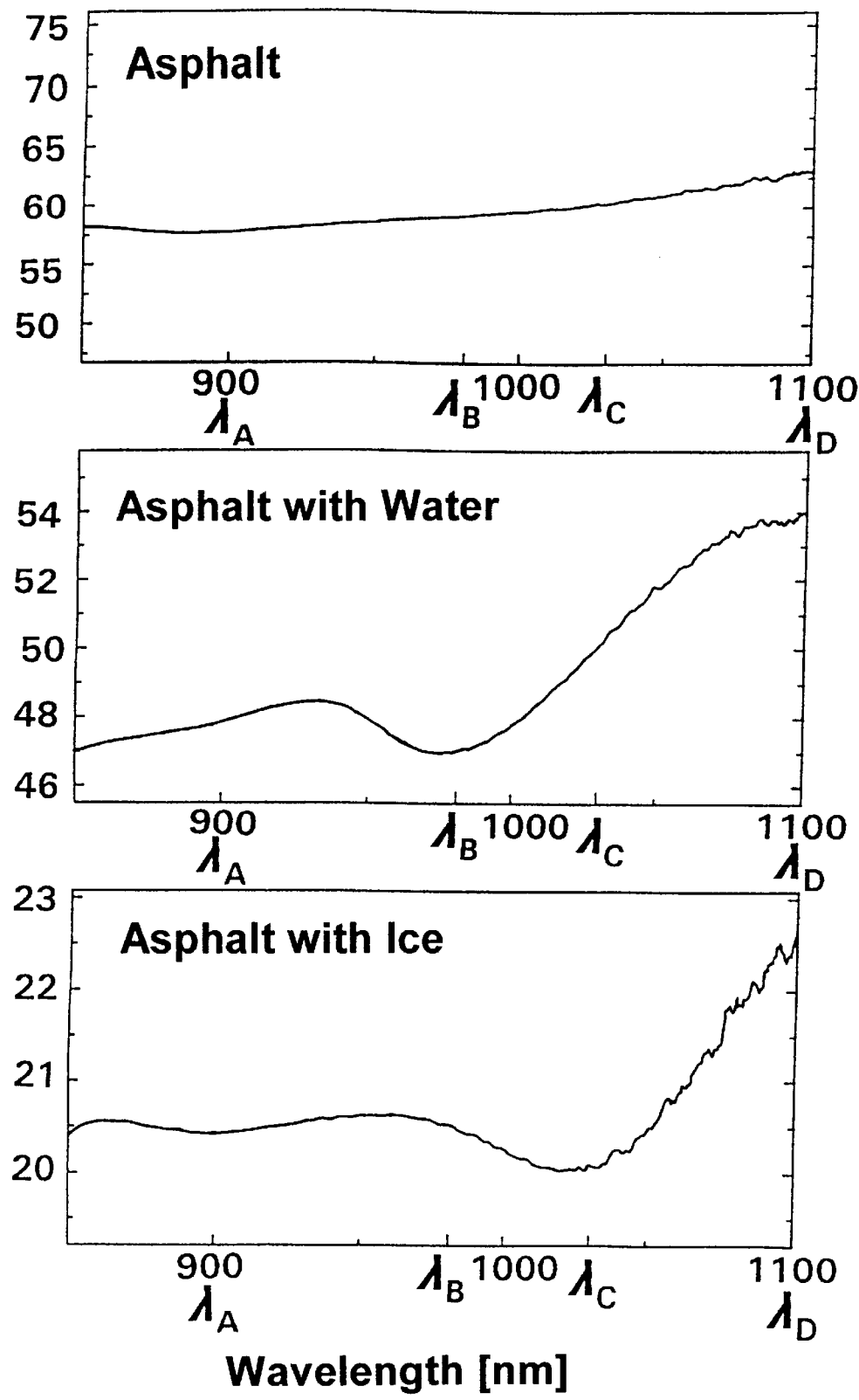

United States Patent [19]

Huth-Fehre et al.

[11] Patent Number: 5,962,853
[45] Date of Patent: Oct. 5, 1999

[54] PROCESS FOR DETERMINING THE SURFACE STATE OF HIGHWAYS IN PARTICULAR, AND DEVICE FOR CARRYING OUT THIS PROCESS

[75] Inventors: Thomas Huth-Fehre; Karl Cammann; Thomas Kantimm, all of Muenster, Germany

[73] Assignee: Institut Fuer Chemo- und Biosensorik Muenster E.V., Muenster, Germany

[21] Appl. No.: 08/894,606

[22] PCT Filed: Feb. 23, 1996

[86] PCT No.: PCT/DE96/00347

§ 371 Date: Oct. 22, 1997

§ 102(e) Date: Oct. 22, 1997

[87] PCT Pub. No.: WO96/26430

PCT Pub. Date: Aug. 29, 1996

[30] Foreign Application Priority Data

Feb. 24, 1995 [DE] Germany .......................... 195 06 550

[51] Int. Cl.[6] ...................................................... G01N 21/55
[52] U.S. Cl. .................................... 250/339.11; 250/341.8
[58] Field of Search ............................. 250/339.11, 341.8

[56] References Cited

U.S. PATENT DOCUMENTS

| | | |
|---|---|---|
| 4,274,091 | 6/1981 | Decker . |
| 4,840,706 | 6/1989 | Campbell .......................... 250/339.11 |
| 5,180,122 | 1/1993 | Christian et al. . |
| 5,218,206 | 6/1993 | Schmitt et al. ..................... 250/339.11 |

FOREIGN PATENT DOCUMENTS

| | | |
|---|---|---|
| 2712199 | 9/1978 | Germany . |
| 4008280 | 9/1991 | Germany . |
| 58-105024 | 6/1983 | Japan . |
| 63-42429 | 2/1988 | Japan . |
| 63-106530 | 5/1988 | Japan . |

*Primary Examiner*—Constantine Hannaher
*Assistant Examiner*—Andrew Israel
*Attorney, Agent, or Firm*—Marshall & Melhorn

[57] ABSTRACT

There are proposed a method and a device for ascertaining the surface condition, particularly of traffic routes, as regards dryness, wetness or icing, in which the surface is irradiated by a radiation source with an infrared component, and the reflected radiation is measured simultaneously in different wavelength ranges characterizing water and ice. In this case at least four wavelength ranges are selected, permitting sufficient depth or penetration of the radiation into the surface. A first and a second wavelength range are so selected that they are influenced to a very small degree by absorption of the water molecules, and a third and fourth wavelength ranges are so selected that they are characteristic for water and ice. The influence of the background on signals measured in the third and fourth wavelength ranges is compensated for by means of the information in the signals measured in the first and second wavelength ranges. In dependence on the measured signals, therefore, a prediction can be made regarding the surface condition.

9 Claims, 2 Drawing Sheets

PROCESS FOR DETERMINING THE SURFACE STATE OF HIGHWAYS IN PARTICULAR, AND DEVICE FOR CARRYING OUT THIS PROCESS

The device relates to a method of ascertaining the surface condition, particularly of traffic routes, according to the preamble to the main claim, and to a device for carrying out the method.

There is known from DE 40 08 280 a method for non-contacting determination of the road surface condition as regards dryness, wetness or icing, in which the surface to be tested is illuminated by a broad-band light source, and the reflected light is simultaneously selectively measured in two wavelength ranges. The measuring wavelengths in this case lie in a wavelength range in which the reflective behaviour reveals a spectral dependence on the surface condition, i.e. in the wavelength range from 2700 nm to 3200 nm, there being formed from the signals at two wavelengths of this wavelength range a quotient which characterises the surface condition. The respectively determined signal quotient is associated with one of the conditions dry, wet or iced.

The known method has the disadvantage that only the direct surface is considered and not the condition directly beneath the surface. Consequently, over- or under-freezing wetness cannot be recognised, as at the wavelengths of 2700 nm to 3200 nm the depth of penetration of the electromagnetic radiation into the surface is extremely low. In particular, the publication also states that an indication of the surface condition is to be obtained independently of the layer thickness.

The object underlying the invention is to provide a method of ascertaining the surface condition particularly of traffic routes as regards dryness, wetness or icing and to provide a corresponding device, which is cost-effective to manufacture and enables rapid and precise determination of the surface condition even in deeper layers of the surface.

This object is achieved according to the invention by the characterising features of the main claim in conjunction with the features of the preamble. Advantageous further developments and designs of this solution arise from the sub-claims for the method and also for the device necessary for carrying out the method.

By means of the present method according to the invention it is for the first time possible to recognise practically instantaneously ice and frost formation on solid surfaces such as road coverings, by means of measurement by spectroscopic analysis, even taking into account the layer thickness of the surface, this being in dependence on the respective degree of crystallisation; the liquid need not exclusively be water, but may also be another protic liquid or solution capable of solidification, i.e. for example a saline solution with lowered freezing point. The degree of crystallisation of the water or of the liquid can be determined from the various absorption bands of at least two spectral sections, spectral ranges being selected in which the difference in the reflection spectrum between liquid and solid aggregate condition becomes particularly clear and in which the depth of penetration is sufficiently great, i.e. of the order of magnitude of the water or ice layers normally present on traffic routes. The influence of the background, caused by the depth of penetration required according to the invention, for example of the roadway covering and a scattering of the material, e.g. of the ice of the surface layer, is determined by measurement of the reflected radiation in two further wavelength ranges, which are influenced to a very small degree by an absorption of the molecules of the protic liquid or solution, independently of the degree of crystallisation. This influence is then compensated for in evaluation of the measurement.

It is advantageous to undertake the spectroscopic measurements both in front of and behind a wheel contact surface of a vehicle, and then to set the evaluations in relation to one another, so that further information, for example between slush and ice layers covered with a film of water, can be undertaken.

By means of the measures indicated in the sub-claims, advantageous further developments and improvements are possible.

Figure 2:
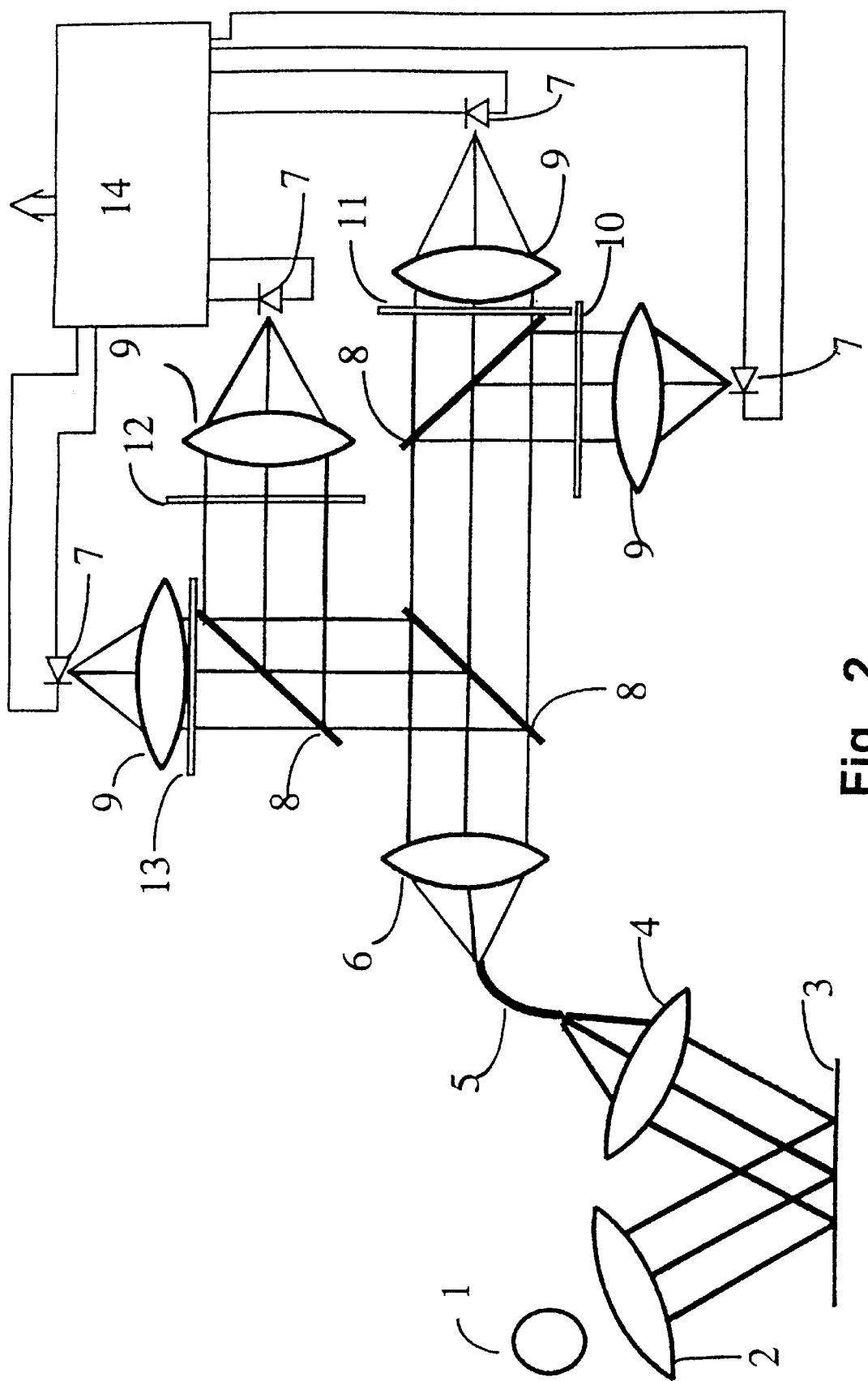

An embodiment of the invention, given by way of example, is shown in the drawing, and is explained in more detail in the following description. Shown are:

FIG. 1: reflective spectra for dry asphalt, asphalt with water and asphalt with ice, and FIG. 2: a schematic view of the device according to the invention.

FIG. 1 shows various reflective spectra for a wavelength range of about 850 nm to 1100 nm, the upper spectrum applying to dry asphalt, the middle spectrum to asphalt with water and the lower spectrum to asphalt with ice. It can be recognised from the spectra that in specific wavelength ranges the spectral values alter with the degree of crystallisation. By measuring these spectral values therefore information can be obtained regarding the degree of crystallisation of a roadway surface. For example, the absorption bands of water among other things lie at about 840 nm, 970 nm, 1170 nm and correspondingly for ice at 890 to 920 nm, 1020 to 1060 nm, 1260 to 1290 nm and so forth.

At these various wavelengths, radiation directed onto a water/ice layer can penetrate layers of different thicknesses before it is absorbed, i.e. the depth of penetration of the electromagnetic radiation into the layers alters with the wavelength. There are given as an example for some wavelengths with water and ice the depths of penetration, the depth of penetration here being understood to mean the depth at which the irradiated light or radiation has dropped to 1/e:

water:

980 nm–2.17 cm;

1200 nm–0.7 cm;

1450 nm–0.035 cm;

1920 nm–0.007 cm;

and at 3000 nm only a few $\mu$m.

Ice:

1030 nm–3.102 cm;

1240 nm–0.72 cm;

1490 nm–0.022 cm;

1980 nm–0.0097 cm;

and at 3000 nm likewise only a few $\mu$m.

It will be recognised from these values that in the high wavelength range, for example of 3000 nm, only an extremely thin surface film can be detected, so that underlying frozen water cannot be detected. In order that a water layer or ice layer can be detected, as is normally present on road surfaces over its entire thickness, measurements must be undertaken at low wavelengths, for example up to 1300 nm. If however the wavelength ranges are selected with sufficient, i.e. at least several millimetres of depth of penetration, during measurement of spectral reflection degrees, the spectral properties of the road covering are also detected. There is given as an example in FIG. 1 the spectral reflective degree of asphalt, the spectral properties being basically dependent on the grain size. For various road surfaces, the spectral of reflective capacity also change; measurements of various road surfaces have however shown that the reflectivity or the degrees of reflection in the wavelength range of interest can be linearly approximated in most relevant cases.

As the spectral properties of the background are also detected during reflective measurements of wet or iced surfaces, they must be compensated for. In order to carry out this compensation, in the method according to the invention reflection measurements are undertaken at two wavelengths which are invariant relative to icing or crystallisation, in order to determine the background, and further reflective measurements are undertaken at two wavelengths which carry the water/ice information. In FIG. 1 the wavelengths for determining the background are identified by $\lambda_A$ and $\lambda_D$ and the wavelengths with water/ice information with $\lambda_B$ and $\lambda_C$.

There will be a discussion in the following of the evaluation of the reflective measurement at the four wavelength ranges. In order to detect the influence of the background, the gradient of the background lines is determined, the signal voltage at the wavelengths being identified by $S(\lambda)$:

$m \approx S(\lambda_D) - S(\lambda_A)$ divided by $\lambda_D - \lambda_A$.

The background signal $S_X$ at the wavelengths $\lambda_B$ and $\lambda_C$ is determined as:

$S_H(\lambda_B) \approx S(\lambda_A) + m(\lambda_B - \lambda_A)$ $S_H(\lambda_C) = S(\lambda_A) + m(\lambda_C - \lambda_A)$ These background signals are derived from the actual signals at $\lambda_B$ and $\lambda_C$ to form signals cleared of background effect:

$S'(\lambda_B) = S(\lambda_B) - S_H(\lambda_B)$ $S'(\lambda_C) = S(\lambda_C) - S_H(\lambda_C)$.

The reflective capacity of the background causes the overall level of the back-scattered light to fluctuate intensely: therefore
$S''(\lambda_B) = S'(\lambda_B)/S_G$ and $S''(\lambda_C) = S'(\lambda_C)/S_G$.

The sums of $S''(\lambda_B)$ and $S''(\lambda_C)$ are a measure for the overall quantity of moisture present, i.e. for all the water molecules present. The difference in the two values $S''(\lambda_B) - S''(\lambda_C)$ and the quotient of the two values $S''(\lambda_B)/S''(\lambda_C)$ are both a measure for the proportion of the material already frozen in the entire quantity of moisture of water molecules. $S''(\lambda_B)$ and $S''(\lambda_C)$ and their sum correlate with the thickness of a water or ice layer, the scattering in the ice being capable of being taken into account during the correlation. Thus the thicknesses of water and/or ice layers can be assessed, even if both are simultaneously present.

An advantageous embodiment of a measuring arrangement for carrying out the method according to the invention is shown schematically in FIG. 2. According to this the electromagnetic radiation of a light or radiation source 1, for example diffuse white light source with an infrared component sufficient for measurement, is passed via an optical condenser system 2 onto the surface to be tested. That proportion of the electromagnetic radiation which is reflected from the surface 3 which, depending on the surface quality, as a rule involves a diffuse reflection, is imaged via an optical collector 4 onto the input surface of an optical wave-guide 5, which for example passes the radiation in a locally precise manner to the receiving and evaluation units, which are disposed for example in the interior of a motor vehicle. the radiation emerging from the optical wave-guide is passed via a second condenser 6 simultaneously to four receivers 7, the radiation being divided between three semi-transparent mirrors 8 with respective 50% reflection and 50% transmission, and projected via collector lenses 9 onto the receivers 7. In this case there are disposed in front of the collector lenses 9 respective wavelength-selective filters 10, 11, 12, 13, which allow passage to the wavelengths $\lambda_A$ to $\lambda_D$ of for example 920, 980, 1030 and 1080 nm.

The receivers 7 are connected to an evaluation unit 14, the evaluation being carried out in accordance with the estimations given above. The output of the evaluation unit, which can be in the form of a microcomputer, is connected to a display unit and/or a warning device. The receivers 7 can be in the form of discrete diodes; also however, rapid-response highly light-sensitive arrays, such for example as diode arrays, CCD arrays or the like can be used. An important factor in measurement is that the entire cross-section of the light beam reflected from the surface 3 to be considered is imaged on each receiver, so that an evaluation can be carried out independently of locus.

The embodiment in FIG. 2 is only an example; it may also be imagined that instead of the semi-transparent mirror 8 and the wavelength-selective filter, a dispersion element in the form of a diffraction lattice or prism may be provided, upon which the radiation is split up in a wavelength-selective manner, the receivers being locally associated, for example via optical wave guides, with the wavelengths on the diffraction lattice.

The evaluation unit 14, independently of the more or less present crystalline condition of the surface 3, i.e. in this case the solid/liquid water, evaluates the reflected spectrum characteristic for this. The evaluation can be carried out in stages according to the above method. However, the evaluation unit 14 can undertake evaluation via corresponding algorithms, carried out on neural networks, together with a logic decision system, based on fuzzy logic, i.e. building on the theory of indefinite quantities, so that in this case there is the possibility of an evaluation with high predictive value even for extremely blurred spectral images. On the basis of the evaluation, water layers of various thicknesses above ice or slush can be detected.

In order to avoid extraneous light and other influencing parameters, intensity modulation of the light source 1 can be undertaken via a chopper wheel or an electronic power control system.

The measuring arrangement according to the invention is disposed on a vehicle preferably in the immediate vicinity of the track. If two such measuring arrangements are provided, one in the direction of travel in front of the track and the other in the direction of travel behind the track, in this way, by means of comparative measurements, conclusions can be reached which if necessary indicate not only skid risk but for example also those risks which can arise due to aquaplaning.

Information can also be supplied by the device according to the invention relating to the micro-roughness of the road covering, as the relationship of the values m determined above (gradient of the spectral curve of the background) and $S_G$ ("median brightness"), is a measure of the wavelength dependency of the scatter capacity of the roadway. The granular size of the scattering particles (Mie-scatter) provides the largest proportion of this wavelength dependency. $m/S_G$ thus identifies the micro-roughness of the road covering which is essential for assessing tyre adhesion to the road. This applies not only with a dry road surface, but for example also in snow, as here also the granular size varies depending on the type of snow.

We claim:

1. A method as ascertaining the surface condition, particularly of traffic routes, with a view to dryness, wetness or icing, in which the surface is irradiated by a radiation source with an infrared component, and the reflected radiation is simultaneously measured in different wavelength ranges characterising water and ice, information on the surface condition being obtained in dependence on the measured signals, wherein the reflected radiation is simultaneously measured selectively in at least four wavelength ranges lying in the area between 800 and 1250 nm, a first and a second wavelength range being so selected that they are influenced to only a small degree by an absorption of the water molecules, independently of the state of aggregation, and a third and fourth wavelength are selected so that they are characteristic for water and ice, and in that an influence of the background, caused by the depth of penetration, on the signals measured in the third and fourth wavelength ranges, is compensated for by means of the information in the signals measured in the first and second wavelength ranges.

2. A method according to claim 1, wherein the third and fourth wavelength ranges are selected between 900 and 110 nm.

3. A method according to claim 1, wherein the proportions of water and ice in the overall quantity of moisture are determined from the ratio and/or the difference in the compensated signals.

4. A method according to claim 1, wherein the overall cross-section of the radiation reflected from the surface is measured independently of locus for each wavelength range.

5. A device of ascertaining the surface condition, particularly of traffic routes, as regards dryness, wetness or icing, with a radiation source with an infrared component for irradiating the surface, an optical condenser system in the beam path in front of the surface to be tested, an optical arrangement collecting the reflected component of the electromagnetic radiation, and a wavelength-selective receiver arrangement, which receives the reflected radiation in accordance with a plurality of wavelength ranges, and an evaluation unit for evaluating the wavelength-selective signals, wherein the receiver arrangement is provided for reception of radiation in four wavelength ranges in a field between 800 and 1250 nm, a first and second wavelength range being so selected that they are influenced to only a small degree by absorption of the water molecules, independently of the state of aggregation, and a third and fourth wavelength range are so selected that they are characteristic for water and ice, and in that the evaluation device is provided in order to compensate for an influence of the background of the signals measured in the third and fourth wavelength ranges by means of the information from the signals measured in the first and second wavelength ranges.

6. A device according to claim 5, wherein the receiver arrangement has three beam-splitters for splitting the reflected radiation into four beam paths of identical locus information and four wavelength-selective filters in front of the respective receivers, which have a transmission band between 800 and 1250 nm.

7. A device according to claim 5, wherein the receiver arrangement has a spatially dispersive element in the form of at least one lattice or prism, which forms a wavelength-selective diffraction spectrum in the wavelength range between 800 and 1250 nm, and that receivers are locally associated with this dispersive element.

8. A device according to claim 5, wherein the receivers are in the form of detector arrays.

9. A device according to claim 5, wherein the device is disposed on vehicles in front of and/or behind a vehicle track.

\* \* \* \* \*